United States Patent [19]
Li et al.

[11] Patent Number: 5,962,268
[45] Date of Patent: Oct. 5, 1999

[54] DNA ENCODING AN IMMUNE CELL CYTOKINE

[75] Inventors: Yi Li, Gaithersburg, Md.; Daniel R. Soppet, Centreville, Va.

[73] Assignee: Human Genome Sciences, Inc., Rockville, Md.

[21] Appl. No.: 08/780,370

[22] Filed: Jan. 9, 1997

Related U.S. Application Data

[60] Provisional application No. 60/009,890, Jan. 11, 1996.
[51] Int. Cl.$^6$ .............................. C12N 15/19; C12N 15/00
[52] U.S. Cl. .................. 435/69.5; 435/69.51; 435/69.52; 435/69.4; 435/69.1; 435/320.1; 435/252.3; 536/23.5
[58] Field of Search ........................... 536/23.5; 435/695, 435/69.51, 69.52, 252.3, 320.1, 69.4

[56] References Cited

U.S. PATENT DOCUMENTS

| | | |
|---|---|---|
| 4,939,093 | 7/1990 | McGrogan et al. . |
| 5,441,871 | 8/1995 | Seon et al. . |

OTHER PUBLICATIONS

Genbank Accession No. U94352 (Jun., 1997).
May, W.A. et al., Nature Genetics, 17:495–497 (Dec., 1997).
Okazaki et al, "IL–7 Promotes Thymocyte Proliferation and Maintains Immunocompetent Thymocytes bearing αβ and γδ T–Cell Receptors In Vitro: Synergism with IL–2." Journal of Immunology, vol. 143, No. 9, Nov. 1, 1989 pp. 2917–2922.
Gillis et al, "Monoclonal Antibody Directed Against Interleukin 2." Journal of Experimental Medicine, vol. 154, Sep. 1981, pp. 983–988.
Zwierina et al, "Practical Aspects of Cytokine Therapy." Stem Cells, vol. 11, 1993 pp. 144–153.
Kollmann et al, "Reconstitutionl of SCID Mice with Human Lymphoid and Myeloid Cells After Transplantation with Human Fetal Bone Marrow Without the Requirement for Exogenous Human Cytokines." Proc. Natl. Acad. Sci. USA, vol. 91, Aug. 1994, pp. 8032–8036.
Gearing et al, "Leukemia Inhibitory Factor Receptor is Structurally Related to the IL–6 Signal Transducer, gp130." EMBO Journal, vol. 10, No. 10, 1991, pp. 2839–2848.
Irvine et al., 1994, Cell 79:595–606.
Neeper et al., 1992, J. Biol. Chem. 267:14998–15004.
Hillier et al., 1995, GenBank Accession No. R65818.
Hillier et al., 1995, GenBank Accession No. R65917.
Hillier et al., 1995, GenBank Accession No. H87611.
Hillier et al., 1995, GenBank Accession No. H29885.
Hillier et al., 1995, GenBank Accession No. H22922.
Trofatter et al., 1995, GenBank Accession No. H55274.
Johnson et al, Development 124, 1997, p. 2245–54 (see sequence alignment).

*Primary Examiner*—Garnette D. Draper
*Attorney, Agent, or Firm*—Kenley K. Hoover

[57] ABSTRACT

Human Immune Cell Cytokine-like Hormone polypeptide and DNA (RNA) encoding such polypeptide in a procedure for producing such polypeptides by recombinant techniques is disclosed. Also disclosed are methods for utilizing such polypeptide for stimulating the proliferation and differentiation of stem cells of the immune system. Antagonists against such polypeptides are also disclosed. The antagonists include antibodies which may be employed as a therapeutic to treat leukemia and lymphoblastoma, may also be used as imaging agents and diagnostic agents for detecting expression levels of the protein. Also disclosed are diagnostic assays for detecting diseases related to mutations in the nucleic acid sequences and altered concentrations of the polypeptides.

28 Claims, 7 Drawing Sheets

FIG. 1A

```
         10         20         30         40         50
1    CTTCCCTCCCACCGCAGCAGCAGTGGCAGAAGCGGGGCTGCCCTTTCTGTGTGCCTCCTTTC  60
         70         80         90        100        110
61   AGCCGGCCTCTGTCTGGGGTTCCCTTCGTCTGGCCCCCGCCCCTGGGCTAAGCGGGGCGGG  120
        130        140        150        160        170
121  GCCAGGCGGTCCCGGAGGCTGCGCAGCAGCCGGACACAGCGGAGCAGGTGGAGACTGGCGG  180
        190        200        210        220        230
181  CGGTCGAGATCGTGCTGCGCCATGGCTCTGGGTCCAGAGCCTCAGCCTCCTACCTCT  240
        250        260        270        280        290
241  TCCCTCCTTGCCAGCCCCTGATGCCCTGCCAGACTTTTGCCTCTGCTGGAGCCCCTGCCTG  300
        310        320        330        340        350
301  ACCAGCTTCCCCTCCCTGTCTGTTGGGATTTGGGGCTGAGCTGTGTGGGGTCCCAGGG  360
        370        380        390        400        410
361  CCAACCAATGCAGTGCCGGCTCCCCGGCGGCCTGGAGCCCTCCTACCCCTGTG  420
-1                    M  Q  C  R  L  P  R  G  L  A  G  A  L  L  T  L  L  C  18
        430        440        450        460        470
421  CATGGGGCTCCTGTGTCTGCGGTACCACTTGAACCTGTCCCGCAGCGGGTACAAGGGAC  480
19     M  G  L  L  C  L  R  Y  H  L  N  L  S  P  Q  R  V  Q  G  T   38
```

MATCH WITH FIG. 1B

FIG. 1B

MATCH WITH FIG. 1A

```
481  CCCGAGCTGAGCCAGCCGAACCCGGGCCCCCTAAGTACAGCTACACGATGTCTTCAT  540
 39   P  E  L  S  Q  P  N  P  G  P  P  K  L  H  D  V  F  I   58

541  TGCAGTGAAGACGACCCGGGCTTTCCACCGCTTGCGCCTGGAGCTGCTGTTGACACGTG  600
 59   A  V  K  T  T  R  A  F  H  R  L  E  L  L  L  D  T  W   78

601  GGTTTCCAGGACCAGGAGGAACAGAGAACATTTGTCTTCACCGACAGCCCAGACAAAGGCCTCCA  660
 79   V  S  R  T  R  E  Q  T  F  V  F  T  D  S  P  D  K  G  L  Q   98

661  GGAGAGACTGGGGTCCCACCTTGTGGTCACCAACTGCTCCGCGGAACAGCCACCCAGC  720
 99   E  R  L  G  S  H  L  V  V  T  N  C  S  A  E  H  S  H  P  A  118

721  TCTGTCCTGCAAGATGGCTGCTGAGTTCGACACCTTCTTGGCCAGTGGGCTTAGGTGGTT  780
119   L  S  C  K  M  A  A  E  F  D  T  F  L  A  S  G  L  R  W  F  138

781  CTGCCATGTGGACGATGACAACTATGTGAACCCAAGGGCGCTGCTGCAGCTTCTGAGAGC  840
139   C  H  V  D  D  D  N  Y  V  N  P  R  A  L  L  Q  L  L  R  A  158

841  CTTCCCGCTGGCCCGCGACGTCTATGTGGGAAGGCCCAGCCTGAACCGGCCCATCCATGC  900
159   F  P  L  A  R  D  V  Y  V  G  R  P  S  L  N  R  P  I  H  A  178
```

MATCH WITH FIG. 1C

FIG. IC

MATCH WITH FIG. IB

```
901  CTCAGAGCCACAGCCCCACAACCGACGAGGCTGGTACAGTTCTGGTTTGCCACTGGGGG  960
179   S   E   P   Q   P   H   N   R   T   R   L   V   Q   F   W   F   A   T   G   G   198

961  TGCTGGCTTCTGCATCAATCGCAAACTGGCTTGAAGATGGCTGTGGGCCAGTGGCTC 1020
199   A   G   F   C   I   N   R   K   L   A   L   K   M   A   P   W   A   S   G   S   218

1021 CCGTTTCATGGACACATTGCTCTCATCCGGCTGCCTGATGACTGCACCATGGGCTATAT 1080
219   R   F   M   D   T   S   A   L   I   R   L   P   D   D   C   T   M   G   Y   I   238

1081 CATTGAGTGCAAGCTGGGCGGCCGCCTGCAGCCCAGCCCCCTTTTCACTCCCACCTGA 1140
239   I   E   C   K   L   G   G   R   L   Q   P   S   P   L   F   H   S   H   L   E   258

1141 GACCCTGCAGCTGCTGAGGACTGCACAGGTCTCCAGAACAGGTCACCCTCAGCTACGGTGT 1200
259   T   L   Q   L   L   R   T   A   Q   L   P   E   Q   V   T   L   S   Y   G   V   278

1201 CTTTGAGGGGAAACTCAACGTCATTAAGTTACAGGGCCCCTTCTCCCGGAGGAGACCC 1260
279   F   E   G   K   L   N   V   I   K   L   Q   G   P   F   S   P   E   E   D   P   298

1261 CTCCAGATTCGCTCCCTCCATTGTCTGCTTCTATCCAGATACACCTGGTGTCCCCAGCT 1320
299   S   R   F   R   S   L   H   C   L   L   Y   P   D   T   P   W   C   P   Q   L   318
```

MATCH WITH FIG. ID

FIG. 1D

MATCH WITH FIG. 1C

```
            1330              1350              1370
1321 GGGTGCCCGATGAATCCTGAACTGCTGGGCAAAGGTTGGACAGAGACTTCTGGGTGTGCC 1380
 319  G   A   R   *                                              338

1390              1410              1430
1381 TTGGCTCCCAAGGTGGCACTGTGGGTCCCTGCAAGTGTCTTGTGATAGGCAGTCCCTGG 1440

1450              1470              1490
1441 CAGGGCCTTCGGGTGGTTGGCAAGCCCAGGATCTGAGTGGCAATTGGCACTGAAGGCACC 1500

1510              1530              1550
1501 CCAGCCCCTGGGAGGTGAGTTAGACAGCCCAGGGGACCAGGTGGACCAGGTGGTGGCCA 1560

1570              1590              1610
1561 GAGAGGCTCCAGGGCTAGACTCCCTCAGGAGGCTGAATTGAAAAAGGGCAGGGGGCACT 1620

1630              1650              1670
1621 TGAGCTGGGGGCTCAGGGCTCCTAACCCTTTAGGCAGTGACATGGCCTCTGGGTGG 1680

1690              1710              1730
1681 GGTCTGGCCGTTGGCCCTGGCTAATGTCTCTCAGTGTCATTCCCCTGGGGCTCAAGCGCTGG 1740

1750              1770              1790
1741 GCCGCCCACTCCTGCCTCCCCTCATCGTGTCCCGAGTTCCTGAAGGACATGGGTGAAT 1800
```

MATCH WITH FIG. 1E

FIG. IE

MATCH WITH FIG. ID

```
1801 GATGGCAGAATCCAGGGTCTGCGAGCACCTGCGTGTTGTTGCCAACCAGTCTCCCAAAGCTC 1860
1861 CTTGCTCCCCACCCCTTGCGAACAGGACCAGATTTGTTTGGAGCCTCAGCATGCCGGGC 1920
1921 CCAGATGATGGAGCATAACGGGTCCCAGCCAATTGTGATGANCCTTTTGCTCATTCCC 1980
1981 AGCCTTTCTTGCTGTTAGGGCTACCAGCTCTGGCCAGAGGGAACTAAGCAA 2040
2041 ATCCAATAGAGATGTTTCTGGGGAAGGTTTTGCAGCCCACTCCCCATCTCTCCTGCTATAA 2100
2101 ATGTGGGTGTGATGGCTGGATNTGGGGCAGCCACCTTGCTACCATGAAGGAAAGGCCAAG 2160
2161 ACAATCATCATCCACAGCTATTCCCTCCAGCATCTGGTTCTGTACAAAATTAAATGCTTATT 2220
2221 TGTTTT 2225
```

FIG. 2A

```
  2  QCRLPRGLAGALLTLLCMGLLCLRYHLNLSPQRVQGT..............  38
     |.. .  |:: .| ::  ::::     :|: :|
 77  QPGAGAPAASPTTVIIRKDIRSFNFSDIEVSERPTATLLTELARRSRNGE  126

39  ..PELSQ.....PNPGPPKLQLHDVFIAVKITRAFHRLRLELLLDTWVSRT   82
       :|      ::  |:|  :|| |:||:|||:|| ::|:||:
127  LLRDLSQRAVTATPQPPVTELDDIFISVKTTKNYHDTRLALIKTWFQLA  176

83  REQTFVFTDSPDKGLQERLGSHLVVTNCSAEHSHPALSCKMAAEFDTFLA  132
     |:: |||  :|:    ::|  ||: ||:|:  |:: || :::|:|:|:
177  RDQTWFFTDIDDHYYQEKTKGHLINTKCSQGHFRKALCCKMSAELDVFLE  226

133  SGLRWFCHVDDDNYVNPRALLQLLRAFPLARDVYVGRPSLNRPIHAS.EP  181
     ||:::|||.|||||||||:|::|::|| ::  :|  |:: ::||: | 
227  SGKKWFCHFDDDNYVNVPRLVKLLDEYSPSVDWYLGKPSISSPLEIHLDS  276
```

MATCH WITH FIG. 2B

FIG. 2B

MATCH WITH FIG. 2A

```
182 QPHNRTRLVQFWFATGGAGFCINRKLALKMAPWASGSRFMDTSALIRLPD 231
        :   |||||||||||||||| :|:|:   |:|:::  ||:||
277 KNTTNKKITFWFATGGAGFCLSRALTLKMLPIAGGGKFISIGDKIRFPD 326

232 DCTMGYIIECKLGGRLQPSPLFHSHLETLQLLRTAQLPEQVTLSYGVFEG 281
    |:|||| ||: :|  |   |||||||||:|  | ::|||: |:
327 DVIMGFIIEHLLKVPLTVVDNFHSHLEPMEFIRQDTFQDQVSFSYAHMKN 376

282 KLNVIKLQGPFSPEEDPSRFRSLHCLLYPDTPWCPQ 317
    :||||| |  :       ||||:||| |:   |:
377 QWNVIKVDG.FDMKTDPKRFYSLHCQLFPYFSFCPP 411
```

DNA ENCODING AN IMMUNE CELL CYTOKINE

This application claims benefit under 35 U.S.C. § 119(e) to U.S. Provisional Application Ser. No. 60/009,890, filed Jan. 11, 1996.

This invention relates to newly identified polynucleotides, polypeptides encoded by such polynucleotides, the use of such polynucleotides and polypeptides, as well as the production of such polynucleotides and polypeptides. The polypeptide of the present invention has been putatively identified as a cytokine, more particularly, the polypeptide of the present invention has been identified as an immune cell cytokine-like potential hormone, sometimes hereinafter referred to as "HLHDC84". The invention also relates to inhibiting the action of such polypeptides.

BACKGROUND OF THE INVENTION

The cytokine family of proteins exhibit a wide variety of functions. A hallmark feature is their ability to elicit chemotactic migration of distinct cell types, including polymorphonuclear cells and macrophages. Many cytokines have pro-inflammatory activity and are involved in multiple steps during inflammatory reactions. In addition to their involvement in inflammation, cytokines have been shown to exhibit other activities. For example, interleukin-8 (IL-8) promotes proliferation of keratinocytes.

In light of the diverse biological activities, it is not surprising that cytokines have been implicated in a number of physiological and disease conditions, including lymphocyte trafficking, wound healing, hematopoietic regulation and immunological disorders such as allergy, asthma and arthritis.

The protein of the present invention is a secreted protein, similar to cytokine proteins, and is most homologous at the amino acid level to the fringe (fng) gene of Drosophila.

The fringe (fng) gene, encodes a molecule that mediates signaling between distinct cell populations (Irvine, K. D. and Wieschaus, E., Cell, 79: 595–506 (1994). The fng gene encodes a putatively secreted protein, and mediates processes that establish the wing margin and promote wing outgrowth without otherwise affecting dorsal-ventral wing cell identity.

The fng cDNA includes a 412 codon open reading frame encoding for a novel protein. Notably, this predicted protein product includes a signal sequence at its amino-terminal end but lacks predicted transmembrane domains, suggesting that it is secreted (Kyte J. and Doolittle, R. F., J. Mol. Biol., 157: 105–132 (1982); Eisenberg, D., et al., J. Mol. Biol., 179: 125–142 (1984); von Heijne, G., Nucl. Acids Res. 14: 4583–4690 (1986)). fng may have a role in cell-cell interactions promoting wing margin formation and wing growth. The fng gene affects a class of epithelial cells which ultimately form the wing. This is done by altering the differentiation state of the cells and enhancing their proliferation.

SUMMARY OF THE INVENTION

In accordance with one aspect of the present invention, there are provided novel polypeptides as well as biologically active and diagnostically or therapeutically useful fragments, analogs and derivatives thereof.

In accordance with another aspect of the present invention, there are provided isolated nucleic acid molecules encoding such polypeptides, including mRNAs, cDNAs, genomic DNA as well as biologically active and diagnostically or therapeutically useful fragments, analogs and derivatives thereof.

In accordance with another aspect of the present invention there is provided an isolated nucleic acid molecule encoding a mature polypeptide expressed by the DNA contained in ATCC Deposit No. 97351.

In accordance with another aspect of the present invention there are provided nucleic acid probes comprising nucleic acid molecules of sufficient length to specifically hybridize to sequences of the present invention.

In accordance with yet a further aspect of the present invention, there is provided a process for producing such polypeptides by recombinant techniques which comprises culturing recombinant prokaryotic and/or eukaryotic host cells, containing a nucleic acid sequence of the present invention, under conditions promoting expression of said protein and subsequent recovery of said protein.

In accordance with yet a further aspect of the present invention, there is provided a process for utilizing such polypeptides, or polynucleotides encoding such polypeptides for therapeutic purposes, for example, to stimulate the proliferation, mobilization and differentiation of stem cells in the immune system for autologous transplant and for treating auto-immune disorders, to stimulate growth factor activity and neuronal re-growth and to treat inflammatory disorders.

In accordance with yet a further aspect of the present invention, there are provided antibodies against such polypeptides and a method of employing such antibodies to limit cellular proliferation or induced differentiation of stem cells for the purpose of treating and/or preventing leukemia and lymphoblastoma and as a diagnostic to detect cancer.

In accordance with yet another aspect of the present invention, there are provided antagonists to such polypeptides, which may be used to inhibit the action of such polypeptides, for example, in the treatment of leukemia or lymphoblastoma, arthritis and as adjunct treatment during chemotherapy.

In accordance with another aspect of the present invention there is provided a method of diagnosing a disease or a susceptibility to a disease related to a mutation in the nucleic acid sequences and the protein encoded by such nucleic acid sequences.

In accordance with another aspect of the present invention there is provided a method of delivering the polynucleotide of the present invention to cells of a patient, either ex vivo or in vivo, such that the gene product of the present invention is administered to the patient.

In accordance with yet a further aspect of the present invention, there is provided a process for utilizing such polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

BRIEF DESCRIPTION OF THE FIGURES

The following drawings are illustrative of embodiments of the invention and are not meant to limit the scope of the invention as encompassed by the claims.

FIGS. 1A–E displays the cDNA sequence (SEQ ID NO:1) and corresponding deduced amino acid sequence of the HLHDC84 polypeptide (SEQ ID NO:2) of the present invention. The underlined portion represents a putative leader sequence of 20 amino acid residues. The standard one-letter abbreviations for amino acids are used. Sequencing was performed using a 373 Automated DNA sequencer (Applied Biosystems, Inc.).

FIGS. 2A–B is an illustration of amino acid sequence homology between the protein polypeptide of the present invention (SEQ ID NO:2) and the Drosophila fringe protein (SEQ ID NO:9).

DETAILED DESCRIPTION OF THE INVENTION

In accordance with an aspect of the present invention, there are provided isolated nucleic acids (polynucleotides) which encode for the mature polypeptides having the deduced amino acid sequences of FIGS. 1A–E (SEQ ID No:2).

The polynucleotide encoding the polypeptide of the present invention was isolated from a human fetal lung cDNA library. Based on results of Northern Blot analyses the polypeptide of the present invention is located primarily in tissues of the bloodstream. The polypeptide contains an open reading frame encoding a protein of 321 amino acids wherein the first 20 amino acids are a putative leader sequence such that the mature protein comprises 301 amino acids. The protein exhibits the highest degree of homology at the amino acid level to the Drosophila fringe protein (SEQ ID NO:9) with 42.222% identity and 61.270% similarity.

In accordance with another aspect of the present invention there are provided isolated polynucleotides encoding a mature polypeptide expressed by the human cDNA contained in ATCC Deposit No. 97351, deposited with the American Type Culture Collection, 12301 Park Lawn Drive, Rockville, Md. 20852, USA, on Nov. 28, 1995. The deposited material is an E. Coli host harboring a pBluescript SK (−) vector (Stratagene, La Jolla, Calif.) which contains the full-length HLHDC84 cDNA.

The deposit(s) will be maintained under the terms of the Budapest Treaty on the International Recognition of the Deposit of Micro-organisms for purposes of Patent Procedure. The strain will be irrevocably and without restriction or condition released to the public upon the issuance of a patent. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptides may be identical to the coding sequences shown in FIGS. 1A–E (SEQ ID NO:1) or may be a different coding sequence which coding sequence, as a result of the redundancy or degeneracy of the genetic code, encodes the same mature polypeptides as the DNA of FIGS. 1A–E (SEQ ID NO:1).

The polynucleotides which encode for the mature polypeptides of FIGS. 1A–E (SEQ ID NO:2) may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptides.

Thus, the term "polynucleotide encoding a polypeptide" encompasses a polynucleotide which includes coding sequence for the polypeptide and may also include additional coding and/or non-coding sequence such as introns.

The present invention further relates to variants of the hereinabove described polynucleotides which encode for fragments, analogs and derivatives,of the polypeptide having the deduced amino acid sequences of FIGS. 1A–E (SEQ ID NO:2). The variant of the polynucleotides may be a naturally occurring allelic variant of the polynucleotides or a non-naturally occurring variant of the polynucleotides.

Thus, the present invention includes polynucleotides encoding the same mature polypeptides as shown in FIGS. 1A–E (SEQ ID NO:2) as well as variants of such polynucleotides which variants encode for a fragment, derivative or analog of the polypeptides of FIGS. 1A–E (SEQ ID NO:2). Such nucleotide variants include deletion variants, substitution variants and addition or insertion variants.

As hereinabove indicated, the polynucleotides may have a coding sequence which is a naturally occurring allelic variant of the coding sequences shown in FIGS. 1A–E (SEQ ID NO:1). As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptides may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotides of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptides of the present invention. The marker sequence may be a hexa-histidine tag supplied by a pQE vector (Qiagen, Inc.) to provide for purification of the mature polypeptides fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37: 767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type have at least 15 bases, preferably at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides whichhybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNA of FIGS. 1A–E (SEQ ID NO:1).

Alternatively, the polynucleotide may have at least 15 bases, preferably at least 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 and polynucleotides complementary thereto as well as portions thereof, which portions have at least 15 consecutive bases and preferably at least 30 consecutive bases and more preferably at least 50 consecutive bases and to polypeptides encoded by such polynucleotides.

The present invention further relates to polypeptides which have the deduced amino acid sequences of FIGS. 1A–E (SEQ ID NO:2), as well as fragments, analogs and derivatives of such polypeptides.

The terms "fragment," "derivative" and "analog" when referring to the polypeptides of FIGS. 1A–E (SEQ ID NO:2) means polypeptides which retain essentially the same biological function or activity as such polypeptides. Thus, an analog includes a proprotein which can be activated by cleavage of the proprotein portion to produce an active mature polypeptide.

The polypeptides of the present invention may be recombinant polypeptides, natural polypeptides or synthetic polypeptides, preferably recombinant polypeptides.

The fragment, derivative or analog of the polypeptides of FIGS. 1A–E (SEQ ID NO:2) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E.$ $coli$, lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline-or ampicillin resistance in $E.$ $coli.$ The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as $E.$ $coli$, Streptomyces, $Salmonella$ $typhimurium$; fungal cells, such as yeast; insect cells such as Drosolhila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pBluescript SK, pBSKS, pNH8A, pNH16a, pNH18A, pNH46A (Stratagene); pTRC99a, pKK223-3, pKK233-3, pDR540, pRIT5 (Pharmacia). Eukaryotic: pWLNEO, pSV2CAT, pOG44, pXT1, pSG (Stratagene) pSVK3, PBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene products encoded by the recombinant sequences. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of $E.$ $coli$ and $S.$ $cerevisiae$ TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23: 175 (1981), and other cell lines capable of expressing a compatible vector, for example, the C127, 3T3, CEO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The HLHDC84 polypeptide may be employed to stimulate the proliferation, mobilization and differentiation of stem cells. Accordingly, it may be employed to treat autoimmune diseases and for autologous transplant.

The polypeptide of the present invention may also be employed to treat and/or prevent inflammation.

The polypeptide of the present invention may also be employed to stimulate neuronal re-growth for the regeneration of nerves, and as a research reagent.

The polynucleotides and polypeptides encoded by such polynucleotides may also be utilized for in vitro purposes related to scientific research, synthesis of DNTA and manufacture of DNA vectors and for designing therapeutics and diagnostics for the treatment of human disease.

Fragments and analogs and derivatives of the polypeptide of the present invention may be identified by assays which detect chemotactic activity. One example of such an assay comprises testing such polypeptides for chemotactic activities toward murine polymorphonuclear cells (PMN) or macrophages, human PMN (isolated on mono-poly-resolving medium; FLOW, McLean, Va.). Conditioned medium (diluted and fully supplemented Dulbecco's Modified Eagles medium) and cell lysates (diluted and supplemented Dulbecco's Modified Eagles medium containing 0.1% BSA instead of 10% FCS) from transiently transfected CV-1 cells are tested for chemotactic activities toward murine PMNs. Endotoxin content of media and all solutions to be tested are measured using a chromogenic limulus amoebocyte lysate assay (Cape Cod Associates, Woods Hole, Mass.), which was sensitive to 5 pg endotoxin/ml. Chemotactic activity is defined as the mean number of cells migrating through the pores of the membrane in 3 to 5 standard fields and quantified by image analysis (Wild-Leitz, Rockleigh, N.J.) using planimetry measurements (magnification times 100) or by counting normally. Endotoxin-activated mouse serum (5%) or FMLP($10^{-7}$M) are used as positive controls.

This invention is also related to the use of the HLHDC84 gene as part of a diagnostic assay for detecting diseases or susceptibility to diseases related to the presence of mutations in the HLHDC84 nucleic acid sequences. Such diseases are related to under-expression of human HLHDC84 polypeptides, for example, lack of proliferation and differentiation of stem cells which may lead to immune disorders.

Individuals carrying mutations in the HLHDC84 gene may be detected at the DNA level by a variety of techniques. Nucleic acids for diagnosis may be obtained from a patient's cells, including but not limited to blood, urine, saliva, tissue biopsy and autopsy material. The genomic DNA may be used directly for detection or may be amplified enzymatically by using PCR (Saiki et al., Nature, 324: 163–166 (1986)) prior to analysis. RNA or cDNA may also be used for the same purpose. As an example, PCR primers complementary to the -nucleic acid encoding HLHDC84 polypeptide can be used to identify and analyze HLHDC84 mutations. For example, deletions and insertions can be detected by a change in size of the amplified product in comparison to the normal genotype. Point mutations can be identified by hybridizing amplified DNA to radiolabeled HLHDC84 RNA or alternatively, radiolabeled HLHDC84 antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230: 1242 (1985)).

Sequence changes at specific locations may also be revealed by nuclease protection assays, such as RNase and S1 protection or the chemical cleavage method (e.g., Cotton et al., PNAS, USA, 85: 4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of HLHDC84 polypeptide in various tissues since an altered expression of the proteins compared to normal control tissue samples may detect the presence of a disease or susceptibility to a disease, for example, malignancies such as cancers and tumors. Assays used to detect levels of HLHDC84 polypeptide in a sample derived from a host are well-known to those of skill in the art and include radioimmunoassays, competitive-binding assays, Western Blot analysis, ELISA assays and "sandwich" assay. An ELISA assay (Coligan, et al., Current Protocols in Immunology, 1(2), Chapter 6, (1991)) initially comprises preparing an antibody specific to an HLHDC84 antigen, preferably a monoclonal antibody. In addition a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g. a polystyrene dish, that binds the proteins in the sample. Any free protein binding sites on the dish are then covered by incubating with a non-specific protein like BSA. Next, the monoclonal antibody is incubated in the dish during which time the monoclonal antibodies attach to any HLHDC84 polypeptide attached to the polystyrene dish. All unbound monoclonal antibody is washed out with buffer. The reporter antibody linked to horseradish peroxidase is now placed in the dish resulting in binding of the reporter antibody to any monoclonal antibody bound to HLHDC84 polypeptide. Unattached reporter antibody is then washed out. Peroxidase substrates are then added to the dish and the amount of color developed in a given time period is a measurement of the amount of HLHDC84 polypeptide present in a given volume of patient sample when compared against a standard curve.

A competition assay may be employed wherein antibodies specific to HLHDC84 polypeptide are attached to a solid support and labeled HLHDC84 polypeptide and a sample derived from the host are passed over the solid support and the amount of label detected, for example by liquid scintillation chromatography, can be correlated to a quantity of HLHDC84 polypeptide in the sample.

A "sandwich" assay is similar to an ELISA assay. In a "sandwich" assay HLHDC84 polypeptide is passed over a solid support and binds to antibody attached to a solid support. A second antibody is then bound to the HLHDC84 polypeptide. A third antibody which is labeled and specific to the second antibody is then passed over the solid support and binds to the second antibody and an amount can then be quantified.

This invention provides a method for identification of the receptors for the human HLHDC84 polypeptides. The gene encoding the receptor can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to the polypeptides, and a cDNA library created from this RNA is divided into pools and used to transfect COS cells or other cells that are not responsive to the polypeptides. Transfected cells which are grown on glass slides are exposed to the labeled polypeptides. The polypeptides can be labeled by a variety of means including iodination or inclusion of a recognition site for a site-specific protein kinase. Following fixation and incubation, the slides are subjected to autoradiographic analysis. Positive pools are identified and sub-pools are prepared and retransfected using an iterative sub-pooling and rescreening process, eventually yielding a single clone-that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

This invention also provides a method of screening compounds to identify antagonists to the HLHDC84 gene and polypeptides of the present invention. Antagonists may be identified by the chemotaxis assay described above.

Examples of potential HLHDC84 polypeptide antagonists include antibodies, or in some cases, oligonucleotides, which bind to the polypeptides. Another example of a potential antagonist is a negative dominant mutant of the polypeptides. Negative dominant mutants are polypeptides which bind to the receptor of the wild-type polypeptide, but fail to retain biological activity.

Antisense constructs prepared using antisense technology are also potential antagonists. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple-helix, see Lee et al., Nucl. Acids Res., 6: 3073 (1979); Cooney et al, Science, 241: 456 (1988); and Dervan et al., Science, 251: 1360 (1991)), thereby preventing transcription and the production of human HLHDC84. The antisense RNA oligonucleotide hybridizes to the mRNA in vivo and blocks translation of the mRNA molecule into the polypeptides (antisense—Okano, J. Neurochem., 56: 560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of human HLHDC84.

Another potential human HLHDC84 antagonist is a peptide derivative of the polypeptides which are naturally or synthetically modified analogs of the polypeptides that have lost biological function yet still recognize and bind to the receptors of the polypeptides to thereby effectively block the receptors. Examples of peptide derivatives include, but are not limited to, small peptides or peptide-like molecules.

The antagonists specific to HLHDC84 may be employed to inhibit and/or limit cellular proliferation or induced differentiation of stem cells of the immune system and may therefore be employed to treat and/or prevent cancers such as leukemia and lymphoblastoma.

The antagonists may be employed to control the proliferation and differentiation of stem cells, particularly in the immune system. This activity may be employed as adjunct protective treatment during cancer chemotherapy by inhibiting bone marrow stem cell colony formation.

The antagonists may also be employed to inhibit the differentiation and proliferation of cells of the immune system to treat and/or prevent arthritis.

The antagonists may be employed in a composition with a pharmaceutically acceptable carrier, e.g., as hereinafter described.

The human HLHDC84 polypeptides and antagonists may be employed in combination with a suitable pharmaceutical carrier. Such compositions comprise a therapeutically effective amount of the polypeptide or antagonist, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides and antagonists may be employed in conjunction with other therapeutic compounds.

The pharmaceutical compositions may be administered in a convenient manner such as by the topical, intravenous, intraperitoneal, intramuscular, intratumor, subcutaneous, intranasal or intradermal routes. The pharmaceutical compositions are administered in an amount which is effective for treating and/or prophylaxis of the specific indication. In general, the polypeptides will be administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

The HLHDC84 polypeptides and antagonists which are polypeptides, may be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19 -17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells. The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

Antibodies specific to the polypeptide of the present invention may be employed as a diagnostic to determine altered levels of the polypeptide in a sample derived from a host by techniques known in the art. Altered levels are indicative of certain disorders, for example, cancer. The expression level of the protein is altered in cancerous cells and an antibody which detects the level of this protein is thus useful as a diagnostic for the state of the disease, prognosis, or as an imaging agent for identifying cancerous cells, wherein the antibody is labeled with a marker capable of detection by a medical imaging machine.

For preparation of monoclonal antibodies, any technique which provides antibodies produced by continuous cell line cultures can be used. Examples include the hybridoma technique (Kohler and Milstein, 1975, Nature, 256: 495–497), the trioma technique, the human B-cell hybridoma technique (Kozbor et al., 1983, Immunology Today 4: 72), and the EBV-hybridoma technique (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The above-described antibodies may be employed to isolate the polypeptide of the present invention by attachment of the antibody to a solid support and performing affinity chromatography by passing the polypeptide desired to be purified over the column and recovering the purified polypeptide.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described. "Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8: 4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase" ) per 0.5 μg of approximately equimolar amounts of the DNA fragments to be ligated.

Unless otherwise stated, transformation was performed as described in the method of Graham, F. and Van der Eb, A., Virology, 52: 456–457 (1973).

EXAMPLE 1
Expression of Recombinant HLHDC84 in COS cells

The expression of plasmid, HLHDC84 is derived from a vector pcDNAI/Amp (Invitrogen) containing: 1) SV40 origin of replication, 2) ampicillin resistance gene, 3) E.coli replication origin, 4) CMV promoter followed by a polylinker region, a SV40 intron and polyadenylation site. A DNA fragment encoding the entire HLHDC84 precursor is cloned into the polylinker region of the vector, therefore, the recombinant protein expression is directed under the CMV promoter.

The plasmid construction strategy is described as follows:
The DNA sequence encoding for HLHDC84, ATCC #97351, is constructed by PCR using two primers: the 5' primer 5' GTCTGGGATCCCAGGGCGAAGCCATG-CAGTGC 3' (SEQ ID NO:5) contains a BamHI site (in bold) followed by 9 nucleotides of HLHDC84 coding sequence starting from the minus 3 position relative to initiation codon; the 3' sequence 5' TCTGTGGATCCTTTGCCCAGC 3' (SEQ ID NO:6) contains complementary sequences to a BamHI site. Therefore, the PCR product contains a BamHI site, HLHDC84 coding sequence and a second BamHI site. The PCR amplified DNA fragment and the vector, pcDNAI/Amp, are digested with BamHI restriction enzyme and ligated. The ligation mixture is transformed into E. coli strain SURE (Stratagene Cloning Systems, La Jolla, Calif. ) the transformed culture is plated on ampicillin media plates and resistant colonies are selected. Plasmid DNA is isolated from transformants and examined by restriction analysis for the presence of the correct fragment. For expression of the recombinant HLHDC84, COS cells are transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the HLHDC84 HA protein is detected by radiolabelling and immunoprecipitation method (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media are then collected and cells are lysed with detergent (RIPA buffer (150 mM NaCl, 1% NP-40, 0.1% SDS, 1% NP-40, 0.5% DOC, 50 mM Tris, pH 7.5). (Wilson, I. et al., Id. 37: 767 (1984)). Both cell lysate and culture media are precipitated with a HA specific monoclonal antibody. Proteins precipitated are analyzed by SDS-PAGE.

EXAMPLE 2
Cloning and Expression of HLHDC84 Using the Baculovirus Expression System The DNA sequence encoding the full length HLHDC84 protein, ATCC #97351, is amplified using PCR oligonucleotide primers corresponding to the 5' and 3' sequences of the gene:

The 5' primer has the sequence 5' TGGGATCCCAGGC-CGC CATCATGCAGTGCCGGCTCC 3' (SEQ ID NO:7) and contains a BamHI restriction enzyme site (in bold) followed by 16 nucleotides of coding sequence.

The 3' primer has the sequence 5' GGCTCTAGACCC AGCAGTTCAGGATTCATCG 3' (SEQ ID NO:8) and contains the cleavage site for the restriction endonuclease XbaI and nucleotides complementary to the 3' translated sequence of the HLHDC84 gene and stop codon. The amplified sequences are isolated from a 1% agarose gel using a commercially available kit ("Geneclean," BIO 101 Inc., La, Jolla, Calif.). The fragment is then digested with the endonucleases BamHI and XbaI, then purified again on a 1% agarose gel. This fragment is designated F2.

The vector pA2 (modification of pVL941 vector, discussed below) is used for the expression of the HLHDC84 protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the *Autographa californica* nuclear polyhedrosis virus (AcMNPV) followed by the recognition sites for the restriction endonucleases BamHI and Asp781. The polyadenylation site of the simian virus SV40 is used for efficient polyadenylation. For an easy selection of recombinant viruses the beta-galactosidase gene from *E.coli* is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pA2 such as pAc373, pVL941 and pAcIM1 (Luckow, V. A. and Summers, M. D., Virology, 170: 31–39).

The plasmid is digested with the restriction enzymes BamHI and XbaI and then dephosphorylated using calf intestinal phosphatase by procedures known in the art. The DNA is then isolated from a 1% agarose gel using the commercially available kit ("Geneclean" BIO 101 Inc., La Jolla, Calif.). This vector DNA is designated V2.

Fragment F2 and the dephosphorylated plasmid V2 are ligated with T4 DNA ligase. *E. coli* JM101 cells are then transformed and bacteria identified that contained the plasmid (pBac-HLHDC84) with the HLHDC84 gene using the enzymes BamHI and Asp781. The sequence of the cloned fragment is confirmed by DNA sequencing.

5 µg of the plasmid pBac-HLHDC84 is cotransfected with 1.0 µg of a commercially available linearized baculovirus ("BaculoGold™ baculovirus DNA", Pharmingen, San Diego, Calif.) using the lipofection method (Felgner et al. Proc. Natl. Acad. Sci. USA, 84: 7413–7417 (1987)).

1 µg of BaculoGold™ virus DNA and 5 µg of the plasmid pBac-HLHDC84 are mixed in a sterile well of a microtiter plate containing 50 µl of serum free Grace's medium (Life Technologies Inc., Gaithersburg, Md.). Afterwards 10 µl Lipofectin plus 90 µl Grace's medium are added, mixed and incubated for 15 minutes at room temperature. Then the transfection mixture is added dropwise to the Sf9 (*Spodoptera frugiperda*) insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the viruses are added to the cells and blue stained plaques are picked with the tip of an Eppendorf pipette. The agar containing the recombinant viruses is then resuspended in an Eppendorf tube containing 200 µl of Grace's medium. The agar is removed by a brief centrifugation and the supernatant containing the recombinant baculovirus is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-HLHDC84 at a multiplicity of infection (MOI) of 2. Six hours later the medium is removed and replaced with SF900 II medium minus methionine and cysteine (Life Technologies Inc., Gaithersburg). 42 hours later 5 µCi of $^{35}$S-methionine and 5 µCi $^{35}$S cysteine (Amersham) are added. The cells are further incubated for 16 hours.

The growth medium was harvested on day 4 post-infection. After the removal of baculovirus cells by continuous centrifugation, the supernatant was applied to a cation exchange column (pros HS 50 resin from PerSeptive Biosystem) pre-equilibrated with buffer A (40 mM NaAcetate, 50 mM NaCl, pH 5.5). The column was eluted stepwise with increasing NaCl concentration in the same buffer. The fractions containing HLHDC84 were pooled, diluted with buffer A and applied to another cation exchange column (CM20), followed by a NaCl gradient elution. The combined fractions were further purified by gel filtration chromatography (Superdex 200 or Superdex 75 from Pharmacia Biotech). Human HLHDC84 was finally purified to homogeneity (95%) and concentrated by cation exchange chromatography (CM20) after the gel filtration fractionation.

EXAMPLE 3

Expression via Gene Therapy

Fibroblas are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7: 219–25 (1988)) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+aml2 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the,transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated polynucleotide comprising a member selected from the group consisting of:
   (a) a polynucleotide encoding amino acids 1 to 321 of SEQ ID NO:2,
   (b) a polynucleotide encoding amino acids 2 to 321 of SEQ ID NO:2;
   (c) a polynucleotide encoding amino acids 21 to 321 of SEQ ID NO:2;
   (d) a polynucleotide that hybridizes under stringent conditions to the DNA which encodes SEQ ID NO:2, wherein said polynucleotide encodes a polypeptide which stimulates cell proliferation or differentiation;
   (e) a polynucleotide that hybridizes under stringent conditions to the DNA in SEQ ID NO:1, wherein said polynucleotide encodes a polypeptide which stimulates cell proliferation or differentiation; and
   (f) the complement of (a), (b), (c), (d), or (e).

2. The isolated polynucleotide of claim 1, wherein said member is (a).

3. The isolated polynucleotide of claim 1, wherein said member is (b).

4. The isolated polynucleotide of claim 1, wherein said member is (c).

5. The isolated polynucleotide of claim 1, wherein said member is (d).

6. The isolated polynucleotide of claim 1, wherein said member is (f).

7. The isolated polynucleotide of claim 1, wherein said member is (e).

8. A recombinant vector that contains the polynucleotide of claim 1.

9. A recombinant vector that contains the polynucleotide of claim 1 operably associated with a regulatory sequence that controls gene expression.

10. A genetically engineered host cell that contains the polynucleotide of claim 1.

11. A genetically engineered host cell that contains the polynucleotide of claim 1, operatively associated with a regulatory sequence that controls gene expression.

12. A method for producing an immune cell cytokine polypeptide, comprising;
   (a) culturing the genetically engineered host cell of claim 11, under conditions suitable to produce the polypeptide; and
   (b) recovering said polypeptide.

13. An isolated polynucleotide encoding amino acids 21 to 321 of SEQ ID NO:2 except for at least one conservative amino acid substitution, wherein said polypeptide;
   (a) stimulates cell proliferation; or
   (b) stimulates cell differentiation.

14. The isolated polynucleotide of claim 13, wherein said polypeptide stimulates cell proliferation.

15. The isolated polynucleotide of claim 13, wherein said polypeptide stimulates cell differentiation.

16. An isolated polynucleotide comprising a member selected from the group consisting of:
   (a) a polynucleotide encoding a fill-length immune cell cytokine polypeptide encoded by the human cDNA contained in ATCC Deposit No. 97351;
   (b) a polynucleotide encoding the mature immune cell cytokine polypeptide encoded by the human cDNA contained in ATCC Deposit No. 97351;
   (c) a polynucleotide that hybridizes under stringent conditions to DNA which encodes the polypeptide encoded by the cDNA contained in ATCC Deposit No. 97351, wherein said polynucleotide encodes a polypeptide which stimulates cell proliferation or differentiation;
   (d) a polynucleotide that hybridizes under stringent conditions to the human cDNA contained in ATCC Deposit No 97351, wherein said polynucleotide encodes polypeptide which stimulates cell proliferation or differentiation; and
   (e) a polynucleotide complementary to the polynucleotide of (a), (b), (c), or (d).

17. The isolated polynucleotide of claim 16, wherein said member is (a).

18. The isolated polynucleotide of claim 16, wherein said member is (b).

19. The isolated polynucleotide of claim 16, wherein said member is (c).

20. The isolated polynucleotide of claim 16, wherein said member is (e).

21. The isolated polynucleotide of claim 16, wherein said member is (d).

22. A recombinant vector that contains the polynucleotide of claim 16.

23. A recombinant vector that contains the polynucleotide of claim 16, operably associated with a regulatory sequence that controls gene expression.

24. A genetically engineered host cell that contains the polynucleotide of claim 16.

25. A genetically engineered host cell that contains the polynucleotide of claim 16, operatively associated with a regulatory sequence that controls gene expression.

26. A method for producing an immune cell cytokine polypeptide, comprising;
   (a) culturing the genetically engineered host cell of claim 23, under conditions suitable to produce the polypeptide; and
   (b) recovering said polypeptide.

27. An isolated polynucleotide encoding the mature immune cell cytokine polypeptide encoded by the human cDNA contained in ATCC Deposit No. 97351, except for at least one conservative amino acid substitution, wherein said polypeptide;
   (a) stimulates cell proliferation; or (b) stimulates cell differentiation.

28. An isolated polynucleotide encoding a polypeptide comprising at least 50 contiguous amino acids of the amino acid sequence in SEQ ID NO:2, wherein said polypeptide stimulates cell proliferation or differentiation.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 2225 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 368..1330

(xi) SEQUENCE DESCRIPTION: SEQ ID NO:1:

```
CTTCCTCCCA CCGCAGCAGC TGGCAGAGCG GGGCTGCCCT TTCTGCTGGT GCCTCCTTTC      60

AGCCGCCTCT GTCTGGGGTT CCCTTCGTCT GGCCCCGCCC CTCGGGCTAA GCGGGGCGGG     120

GCCAGGCGGT CCCGGAGGCT GCGGCAGGCC GGACAGCGGG AGCAGGTGGA GGACTGGCGG     180

CGGTCGAGAT CGTGCTGCCA TGGCTCAGCC TCTGGGTCCA GAGCCTCAGC TCCTACCTCT     240

TCCCTCCTTG CCAGCCCCTG ATGCCTGCCA GACTTTTGCC TCTGCTGGAG CCCCTGCCTG     300

ACCAGCTTCC CCTCCCTGTC TGGTTGGGAT TTGGGGGCTG AGCTGTCTGG GGTCCCAGGG     360

CCAACCA ATG CAG TGC CGG CTC CCG CGG GGC CTG GCT GGA GCC CTC CTC       409
        Met Gln Cys Arg Leu Pro Arg Gly Leu Ala Gly Ala Leu Leu
          1               5                  10

ACC CTC CTG TGC ATG GGG CTC CTG TGT CTG CGG TAC CAC TTG AAC CTG       457
Thr Leu Leu Cys Met Gly Leu Leu Cys Leu Arg Tyr His Leu Asn Leu
 15                  20                  25                  30

TCC CCG CAG CGG GTA CAA GGG ACC CCC GAG CTG AGC CAG CCG AAC CCG       505
Ser Pro Gln Arg Val Gln Gly Thr Pro Glu Leu Ser Gln Pro Asn Pro
                 35                  40                  45

GGG CCC CCT AAG CTA CAG CTA CAC GAT GTC TTC ATT GCA GTG AAG ACG       553
Gly Pro Pro Lys Leu Gln Leu His Asp Val Phe Ile Ala Val Lys Thr
             50                  55                  60

ACC CGG GCT TTC CAC CGC TTG CGC CTG GAG CTG CTG CTT GAC ACG TGG       601
Thr Arg Ala Phe His Arg Leu Arg Leu Glu Leu Leu Leu Asp Thr Trp
                 65                  70                  75

GTT TCC AGG ACC AGG GAA CAG ACA TTT GTC TTC ACC GAC AGC CCA GAC       649
Val Ser Arg Thr Arg Glu Gln Thr Phe Val Phe Thr Asp Ser Pro Asp
 80                  85                  90

AAA GGC CTC CAG GAG AGA CTG GGG TCC CAC CTT GTG GTC ACC AAC TGC       697
Lys Gly Leu Gln Glu Arg Leu Gly Ser His Leu Val Val Thr Asn Cys
 95                 100                 105                 110

TCC GCG GAA CAC AGC CAC CCA GCT CTG TCC TGC AAG ATG GCT GCT GAG       745
```

-continued

```
                    Ser Ala Glu His Ser His Pro Ala Leu Ser Cys Lys Met Ala Ala Glu
                                    115                 120                 125

TTC GAC ACC TTC TTG GCC AGT GGG CTT AGG TGG TTC TGC CAT GTG GAC              793
Phe Asp Thr Phe Leu Ala Ser Gly Leu Arg Trp Phe Cys His Val Asp
                130                 135                 140

GAT GAC AAC TAT GTG AAC CCA AGG GCG CTG CTG CAG CTT CTG AGA GCC              841
Asp Asp Asn Tyr Val Asn Pro Arg Ala Leu Leu Gln Leu Leu Arg Ala
            145                 150                 155

TTC CCG CTG GCC CGC GAC GTC TAT GTG GGA AGG CCC AGC CTG AAC CGG              889
Phe Pro Leu Ala Arg Asp Val Tyr Val Gly Arg Pro Ser Leu Asn Arg
        160                 165                 170

CCC ATC CAT GCC TCA GAG CCA CAG CCC CAC AAC CGC ACG AGG CTG GTA              937
Pro Ile His Ala Ser Glu Pro Gln Pro His Asn Arg Thr Arg Leu Val
175                 180                 185                 190

CAG TTC TGG TTT GCC ACT GGG GGT GCT GGC TTC TGC ATC AAT CGC AAA              985
Gln Phe Trp Phe Ala Thr Gly Gly Ala Gly Phe Cys Ile Asn Arg Lys
                195                 200                 205

CTG GCT TTG AAG ATG GCT CCG TGG GCC AGT GGC TCC CGT TTC ATG GAC             1033
Leu Ala Leu Lys Met Ala Pro Trp Ala Ser Gly Ser Arg Phe Met Asp
                210                 215                 220

ACA TCT GCT CTC ATC CGG CTG CCT GAT GAC TGC ACC ATG GGC TAT ATC             1081
Thr Ser Ala Leu Ile Arg Leu Pro Asp Asp Cys Thr Met Gly Tyr Ile
            225                 230                 235

ATT GAG TGC AAG CTG GGC GGC CGC CTG CAG CCC AGC CCC CTC TTT CAC             1129
Ile Glu Cys Lys Leu Gly Gly Arg Leu Gln Pro Ser Pro Leu Phe His
        240                 245                 250

TCC CAC CTG GAG ACC CTG CAG CTG CTG AGG ACT GCA CAG CTC CCA GAA             1177
Ser His Leu Glu Thr Leu Gln Leu Leu Arg Thr Ala Gln Leu Pro Glu
255                 260                 265                 270

CAG GTC ACC CTC AGC TAC GGT GTC TTT GAG GGG AAA CTC AAC GTC ATT             1225
Gln Val Thr Leu Ser Tyr Gly Val Phe Glu Gly Lys Leu Asn Val Ile
                275                 280                 285

AAG CTA CAG GGC CCC TTC TCC CCG GAG GAG GAC CCC TCC AGA TTT CGC             1273
Lys Leu Gln Gly Pro Phe Ser Pro Glu Glu Asp Pro Ser Arg Phe Arg
                290                 295                 300

TCC CTC CAT TGT CTG CTC TAT CCA GAT ACA CCC TGG TGT CCC CAG CTG             1321
Ser Leu His Cys Leu Leu Tyr Pro Asp Thr Pro Trp Cys Pro Gln Leu
            305                 310                 315

GGT GCC CGA TGAATCCTGA ACTGCTGGGC AAAGGTTGGA CAGAGACTTC                     1370
Gly Ala Arg
    320

TGGGTGTGCC TTGGCTCCCA AGGTGGCACT GTGGGTCCCT GGCAAGTGTC TTGTGATAGG           1430

CAGTCCCTGG CAGGGCCTTC GGGTGGTTGG CAAGCCCAGG ATCTGAGTGG CAATTGGCAC           1490

TGAAGGCACC CCAGGCCCCT GGGAGGTGAG TTAGACAGCC CAGGGGACCA GGTGGACCAG           1550

GTGGTGGCCA GAGAGGCTCC AGGGGCTAGA CTCCCTCAGG AGGCTGAATT GAAAAGGGC            1610

AGGGGGCACT TGAGCTGGGC TGGGGCTCAG GGGTCCTAAC CCTTTAGGCA GTGACATGGC           1670

CTCTGGGTGG GGTCTGGCCG TTGGCCCTGG CTAATGTCTC TCAGTCATTC CCCTGGGGCT           1730

CAAGCGCTGG GCCGCCCACT CCTGCCTCCC TCATCTGTGT CCCGAGTTCC TGAAGGGACA           1790

TGGGTGGAAT GATGGCAGAA TCCAGGGTCT GCAGCACCTG CTGTTGTTGC AACCAGTCT            1850

CCCAAAGCTC CTTGCTCCCC ACCCCTTGCG AACAGGACCA GATTTTGTTT GGAGCCTCAG           1910

CATGCCGGGC CCAGATGATG GAGCATAACG GGTCCCAGCC AATTGTGATG ANCCTTTTTG           1970
cTCATTTCCC AGCCTTTCTT GCTGTTAGGG CTACCATGG GACCAGCTCT GGCCAGAGGG            2030

AACTAAGCAA ATCCAATAGA GATGTTTCTG GGGAAGGTTT TGCAGCCCAC TCCCCATCTT           2090

CCTGCTATAA ATGTGGGTGT GATGGCTGGA TNTGGGGCAG CCACCTTGCT ACCATGAAGG           2150
```

AAAGGCCAAG ACAATCATCC ACAGCTATTC CCTCCAGCAT CTGGTTCTGT ACAAAAATTA    2210

AATGCTTATT TGTTT    2225

(2) INFORMATION FOR SEQ ID NO:2:

(i) SEQUENCE CHARACTERISTICS:
        (A) LENGTH: 321 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gln Cys Arg Leu Pro Arg Gly Leu Ala Gly Ala Leu Leu Thr Leu
 1               5                  10                  15

Leu Cys Met Gly Leu Leu Cys Leu Arg Tyr His Leu Asn Leu Ser Pro
             20                  25                  30

Gln Arg Val Gln Gly Thr Pro Glu Leu Ser Gln Pro Asn Pro Gly Pro
         35                  40                  45

Pro Lys Leu Gln Leu His Asp Val Phe Ile Ala Val Lys Thr Thr Arg
     50                  55                  60

Ala Phe His Arg Leu Arg Leu Glu Leu Leu Asp Thr Trp Val Ser
 65                  70                  75                  80

Arg Thr Arg Glu Gln Thr Phe Val Phe Thr Asp Ser Pro Asp Lys Gly
                 85                  90                  95

Leu Gln Glu Arg Leu Gly Ser His Leu Val Val Thr Asn Cys Ser Ala
            100                 105                 110

Glu His Ser His Pro Ala Leu Ser Cys Lys Met Ala Ala Glu Phe Asp
        115                 120                 125

Thr Phe Leu Ala Ser Gly Leu Arg Trp Phe Cys His Val Asp Asp Asp
    130                 135                 140

Asn Tyr Val Asn Pro Arg Ala Leu Leu Gln Leu Leu Arg Ala Phe Pro
145                 150                 155                 160

Leu Ala Arg Asp Val Tyr Val Gly Arg Pro Ser Leu Asn Arg Pro Ile
                165                 170                 175

His Ala Ser Glu Pro Gln Pro His Asn Arg Thr Arg Leu Val Gln Phe
            180                 185                 190

Trp Phe Ala Thr Gly Gly Ala Gly Phe Cys Ile Asn Arg Lys Leu Ala
        195                 200                 205

Leu Lys Met Ala Pro Trp Ala Ser Gly Ser Arg Phe Met Asp Thr Ser
    210                 215                 220

Ala Leu Ile Arg Leu Pro Asp Asp Cys Thr Met Gly Tyr Ile Ile Glu
225                 230                 235                 240

Cys Lys Leu Gly Gly Arg Leu Gln Pro Ser Pro Leu Phe His Ser His
                245                 250                 255

Leu Glu Thr Leu Gln Leu Leu Arg Thr Ala Gln Leu Pro Glu Gln Val
            260                 265                 270

Thr Leu Ser Tyr Gly Val Phe Glu Gly Lys Leu Asn Val Ile Lys Leu
        275                 280                 285

Gln Gly Pro Phe Ser Pro Glu Glu Asp Pro Ser Arg Phe Arg Ser Leu
    290                 295                 300

His Cys Leu Leu Tyr Pro Asp Thr Pro Trp Cys Pro Gln Leu Gly Ala
305                 310                 315                 320

Arg
```

(2) INFORMATION FOR SEQ ID NO:3:

(i) SEQUENCE CHARACTERISTICS:
       (A) LENGTH: 335 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:3:

```
Gln Pro Gly Ala Gly Ala Pro Ala Ala Ser Pro Thr Thr Val Ile Ile
1               5                   10                  15

Arg Lys Asp Ile Arg Ser Phe Asn Phe Ser Asp Ile Glu Val Ser Glu
            20                  25                  30

Arg Pro Thr Ala Thr Leu Leu Thr Glu Leu Ala Arg Arg Ser Arg Asn
        35                  40                  45

Gly Glu Leu Leu Arg Asp Leu Ser Gln Arg Ala Val Thr Ala Thr Pro
    50                  55                  60

Gln Pro Pro Val Thr Glu Leu Asp Asp Ile Phe Ile Ser Val Lys Thr
65                  70                  75                  80

Thr Lys Asn Tyr His Asp Thr Arg Leu Ala Leu Ile Ile Lys Thr Trp
                85                  90                  95

Phe Gln Leu Ala Arg Asp Gln Thr Trp Phe Thr Asp Thr Asp Asp
            100                 105                 110

His Tyr Tyr Gln Glu Lys Thr Lys Gly His Leu Ile Asn Thr Lys Cys
                115                 120                 125

Ser Gln Gly His Phe Arg Lys Ala Leu Cys Cys Lys Met Ser Ala Glu
            130                 135                 140

Leu Asp Val Phe Leu Glu Ser Gly Lys Lys Trp Phe Cys His Phe Asp
145                 150                 155                 160

Asp Asp Asn Tyr Val Asn Val Pro Arg Leu Val Lys Leu Leu Asp Glu
                165                 170                 175

Tyr Ser Pro Ser Val Asp Trp Tyr Leu Gly Lys Pro Ser Ile Ser Ser
            180                 185                 190

Pro Leu Glu Ile His Leu Asp Ser Lys Asn Thr Thr Asn Lys Lys
        195                 200                 205

Ile Thr Phe Trp Phe Ala Thr Gly Gly Ala Gly Phe Cys Leu Ser Arg
210                 215                 220

Ala Leu Thr Leu Lys Met Leu Pro Ile Ala Gly Gly Lys Phe Ile
225                 230                 235                 240

Ser Ile Gly Asp Lys Ile Arg Phe Pro Asp Asp Val Thr Met Gly Phe
            245                 250                 255

Ile Ile Glu His Leu Leu Lys Val Pro Leu Thr Val Val Asp Asn Phe
            260                 265                 270

His Ser His Leu Glu Pro Met Glu Phe Ile Arg Gln Asp Thr Phe Gln
        275                 280                 285

Asp Gln Val Ser Phe Ser Tyr Ala His Met Lys Asn Gln Trp Asn Val
290                 295                 300

Ile Lys Val Asp Gly Phe Asp Met Lys Thr Asp Pro Lys Arg Phe Tyr
305                 310                 315                 320

Ser Leu His Cys Gln Leu Phe Pro Tyr Phe Ser Phe Cys Pro Pro
            325                 330                 335
```

(2) INFORMATION FOR SEQ ID NO:4:

(i) SEQUENCE CHARACTERISTICS:
       (A) LENGTH: 32 base pairs

```
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:4:

GTCTGGGATC CCAGGGCGAA GCCATGCAGT GC                                    32

(2) INFORMATION FOR SEQ ID NO:5:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:5:

TCTGTGGATC CTTTGCCCAG C                                                21

(2) INFORMATION FOR SEQ ID NO:6:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:6:

TGGGATCCCA GGCCGCCATC ATGCAGTGCC GGCTCC                                36

(2) INFORMATION FOR SEQ ID NO:7:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:7:

GGCTCTAGAC CCAGCAGTTC AGGATTCATC G                                     31
```